(12) United States Patent
Arber

(10) Patent No.: US 8,614,301 B2
(45) Date of Patent: Dec. 24, 2013

(54) METHODS OF TREATING CANCER USING ANTI CD24 ANTIBODIES

(75) Inventor: Nadir Arber, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 814 days.

(21) Appl. No.: 12/742,666

(22) PCT Filed: Nov. 13, 2008

(86) PCT No.: PCT/IL2008/001491
§ 371 (c)(1),
(2), (4) Date: May 13, 2010

(87) PCT Pub. No.: WO2009/063461
PCT Pub. Date: May 22, 2009

(65) Prior Publication Data
US 2011/0123522 A1    May 26, 2011

Related U.S. Application Data

(60) Provisional application No. 60/996,383, filed on Nov. 14, 2007.

(51) Int. Cl.
*C07K 16/30* (2006.01)
*C07K 16/46* (2006.01)
*A61K 39/395* (2006.01)

(52) U.S. Cl.
USPC .............. 530/388.85; 530/387.1; 530/387.3; 530/388.1; 530/388.5; 530/391.7; 424/130.1; 424/133.1; 424/135.1; 424/141.1; 424/155.1; 424/156.1; 424/181.1

(58) Field of Classification Search
None
See application file for complete search history.

(56) References Cited

U.S. PATENT DOCUMENTS 6,146,628 A    11/2000 Uckun et al.

FOREIGN PATENT DOCUMENTS

| EP | 0356397 | | 2/1990 |
|---|---|---|---|
| WO | WO 9613524 A1 | * | 5/1996 |
| WO | WO 2006100681 A2 | * | 9/2006 |
| WO | WO 2008/002112 | | 1/2008 |
| WO | WO 2009/063461 | | 5/2009 |

OTHER PUBLICATIONS

Strome et al., The Oncologist, 2007; 12:1084-95.*
Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*

Office Action Dated Dec. 29, 2011 From the Israel Patent Office Re. Application No. 205768 and Its Translation Into English.
Response Dated Apr. 7, 2011 to Communication Pursuant to Article 94(3) EPC of Oct. 21, 2010 From the European Patent Office Re. Application No. 08849493.5.
International Search Report Dated Feb. 17, 2009 From the International Searching Authority Re.: Application No. PCT/IL2008/001491.
Written Opinion Dated Feb. 17, 2009 From the International Searching Authority Re.: Application No. PCT/IL2008/001491.
Froesch et al. "Preparation and Functional Evaluation of New Doxorubicin Immunoconjugates Containing an Acid-Sensitive Linker on Small-Cell Lung Cancer Cells", Cancer Immunology and Immunotherapy, XP002959259, 42(1): 55-63, Jan. 1, 1996. p. 56, 1-h Col., § 4, Tables 1, 2, Figs.3-6.
Sagiv et al. "CD24 Is A New Oncogene, Early at the Multistep Process of Colorectal Cancer Carcinogenesis", Gastroenterology, XP005587457, 131(2): 630-639, Aug. 1, 2006. p. 634, r-h Col., § 6, p. 636, r-h Col., Fig.3.
Sagiv et al. "CD24 Plays an Important Role in the Carcinogenesis Process of the Pancreas", Biomedicine & Pharmacotherapy, XP005605585, 60(6): 280-284, 2006. p. 283, 1-h Col., § 4, Fig.3.
Sagiv et al. "Cd24, A Novel Oncogene in Colorectal (CRC) and Pancreatic (PC) Cancers, Is a Promising Target for Treatment by Monoclonal Antibodies or Introduction of Sirna, In-Vitro and In-Vivo", Gastroenterology, XP008101233, 132(4/Suppl.2): A432-A433: M2013, Apr. 2007. & Digestive Disease Week Meeting/108th Annual Meeting of the American-Gastroenterology-Association, Washington, DC, USA, May 19-24, 2007.
Sagiv et al. "Targeting CD24 for Treatment of Colorectal and Pancreatic Cancer by Monoclonal Antibodies or Small Interfering RNA", Cancer Research, XP002512948, 68(8): 2803-2812, Apr. 2008.
Zangemeister-Wittke et al. "Action of A CD24-Specific Deglycosylated Ricin-A-Chain Immunotoxin in Conventional and novel Models of Small-Cell-Lung-Cancer Xenograft", International Journal of Cancer, XP002512947, 53(3): 521-528, 1993. p. 524, 1-h Col., Figs. 1, 3, 4.
International Preliminary Report on Patentability Dated May 27, 2010 From the International Bureau of WIPO Re.: Application No. PCT/IL2008/001491.
Communication Pursuant to Article 94(3) EPC Dated Jun. 8, 2011 From the European Patent Office Re. Application No. 08849493.5.
Communication Pursuant to Rules 161(1) and 162 EPC Dated Jun. 23, 2010 From the European Patent Office Re. Application No. 08849493.5.
Response Dated Jul. 11, 2010 to Communication Pursuant to Rules 161(1) and 162 EPC of Jun. 23, 2010 From the European Patent Office Re. Application No. 08849493.5.
Response Dated Oct. 11, 2011 to Communication Pursuant to Article 94(3) EPC of Jun. 8, 2011 From the European Patent Office Re. Application No. 08849493.5.
Communication Pursuant to Article 94(3) EPC Dated Oct. 21, 2010 From the European Patent Office Re. Application No. 08849493.5.
Communication Pursuant to Article 94(3) EPC Dated Nov. 10, 2011 From the European Patent Office Re. Application No. 08849493.5.
Communication Pursuant to Article 94(3) EPC Dated Dec. 5, 2012 From the European Patent Office Re. Application No. 08849493.5.

* cited by examiner

*Primary Examiner* — Sheela J Huff
*Assistant Examiner* — Jessica H Roark

(57) ABSTRACT

Anti-CD24 antibodies and adjuvant combinations thereof with chemotherapeutic agents or toxins, which can be used to inhibit growth of CD24-expressing cancer cells and prevent and treat cancer are provided.

19 Claims, 6 Drawing Sheets
(4 of 6 Drawing Sheet(s) Filed in Color)

METHODS OF TREATING CANCER USING ANTI CD24 ANTIBODIES

RELATED APPLICATIONS

This Application is a National Phase of PCT Patent Application No. PCT/IL2008/001491 having International filing date of Nov. 13, 2008, which claims the benefit of U.S. Provisional Patent Application No. 60/996,383 filed on Nov. 14, 2007. The contents of the above Applications are all incorporated herein by reference.

FIELD AND BACKGROUND OF THE INVENTION

The present invention, in some embodiments thereof, to compositions and methods for preventing and treating growth of abnormally growing cells using anti-CD24 monoclonal antibodies, and more particularly, to the use of anti-CD24 in combination with cytotoxic chemotherapeutic agents for prevention and treatment of colorectal and pancreatic cancers.

CD24:

CD24 has been described in a growing body of literature in relation to cancer, over-expressed in various human malignancies. Its expression is often correlated with a poor prognosis. Recently, using gene expression array, increased expression of CD24 in transformed, but not non-transformed, enterocytes that was down regulated to a normal level of expression following short (72 hours) and long (six months) exposures to a selective COX2 inhibitor, celecoxib (Celebrex, Pfizer, NY) was observed. The results were validated by immunohistochemical stainings in 389 human samples derived from a variety of GI malignancies. A strong membrane expression of CD24 protein was seen already at an early stage of carcinogenesis, the adenomatous polyp. CD24 was expressed in 90.7% of adenomas, and 86.3% of CRC cases, while very low levels of expression were observed in normal epithelium. The upregulation of CD24 during colorectal cancer (CRC) progression, and its downregulation by a known chemopreventive agent (COX2 inhibitor) suggested the possibility that CD24 could be important in the oncogenic pathway.

The CD24 gene encodes a heavily glycosylated cell-surface protein, anchored to the membrane by phosphatidylinositol. Human CD24 consists of 31 amino acids with 16 potential O- and N-glycosylation sites. CD24 plays a crucial role in cell selection and maturation during hematopoiesis. It is expressed mainly on premature lymphocytes, certain epithelial and neural cells. It also plays a role during the embryonal development of neural and pancreatic cells. Analysis of biochemically separated glycolipid-enriched membrane (GEM) fractions indicated enhanced association of CD24 and Lyn protein tyrosine kinase in GEM, as well as increased Lyn kinase activity after CD24 cross-linking, suggesting that the CD24 receptor mediates intracellular signaling even though it has no trans-membrane domain. CD24 is also known to be an alternative ligand for P-selectin and thus might function in metastases shedding. Anti-CD24 monoclonal antibodies (mAb) induced growth inhibition in lymphocytes precursors.

Studies have shown that CD24 expression could potentiate homotypic B-cell aggregation and heterotypic adhesion to activated endothelium. Under physiological conditions, CD24 over-expression enhanced cancer cells rolling on and invading through vessel-walls by increasing their adherence to platelets and endothelial cells. Thus, within the tumor micro-environment, CD24 binding with P-selectin enhances tumor development, since P-selectin was found to be crucial in CRC carcinogenesis. In P-selectin deficient mice vs. normal mice, human CRC cells injected subcutaneously into mice proliferated more slowly and produced fewer lung metastases at intra-venous injection, suggesting that the mucin-dependent interaction with P-selectin is an important feature of CRC cells.

Bauman et al. showed that ectopic over-expression of CD24 in a rat-carcinoma cell line increases cell proliferation and adhesion through activation of integrins. Similarly, Smith et al. have shown how transient down-regulation of CD24 expression in human carcinoma cell lines resulted in growth inhibition and reduced clonogenicity and cell migration through a change in the actin cytoskeleton in several epithelial cancer cell lines (breast, urothelial and prostate carcinomas and osteosarcoma).

Patents and patent applications relating to CD24 and cancer include: U.S. Pat. No. 7,115,360 to Clarke et al; U.S. Pat. No. 6,984,522 to Clarke et al.; U.S. Pat. No. 6,171,798 to Levine et al; U.S. Pat. No. 5,952,471 to Lawson; U.S. Pat. No. 6,146,628 to Uckun et al.; U.S. patent application Ser. No. 12/033,557 to Agarwal; U.S. patent application Ser. No. 10/913,905 to Hsing-Chang et al; U.S. patent application Ser. No. 12/019,339 to Wicha et al; and U.S. patent application Ser. No. 11/607,780 to Clarke et al.

Colorectal Cancer:

Colorectal cancer (CRC) represents a major public health problem accounting for over 1 million cases of new cancers and about half a million deaths worldwide. Despite curative surgery in those presenting early, the risk of recurrence is significantly high. In colon cancer, chemotherapy is the principal adjuvant therapy and the addition of radiotherapy to chemotherapy has not been shown to improve outcome. Recently, newer drugs with significant impact in the treatment of metastatic CRC such as irinotecan, oxaliplatin and oral fluoropyrimidines have all completed phase III randomised testing in the adjuvant setting of colon cancer.

Antibody Anti-Cancer Therapy:

There are many potential advantages to the application of antibodies to anti-cancer treatment. Antibodies are typically much more specific in targeting cancerous cells than metabolic drugs or radiotherapy, and as such typically have fewer and less sever side effects. In addition, monoclonal antibodies can be designed to target antigens characteristic of individual stages or forms of cancers, affording opportunity to customize therapy to the individual patient's disease profile.

Many clinical trials of anti-cancer antibody therapy have been undertaken, indicating good outcomes with fewer side effects as compared to chemotherapy or radiotherapy. A growing number of therapeutic monoclonal antibodies have been approved for clinical use by the FDA, such as Ritaximab, Ibritumomab and Tositumomab for Non-Hodgkins Lymphoma, Trastuzumab for Breast Cancer, Gemtuzumab for AML, Alemtuzumab for CLL, and Cetuximab, Bevacizumab and Panitumumab for colorectal, non-small cell lung cancer and head and neck cancer. A few of these approved anti-cancer antibodies are conjugated antibodies, such as Ibritumomab and Tositumomab, which are radio-conjugates, and Gemtuzumab, which is an immunotoxin conjugated to the toxin ozagamicin.

Combination (Adjuvant) Therapy:

Modern cancer treatment protocols often combine more than one modality in order to both benefit from targeting of multiple aspects of the disease and reduction in dosage or duration of individual treatments, resulting in reduced frequency and severity of side effects. Combined chemotherapy and radiotherapy, or "cocktails" of chemotherapy drugs are commonly prescribed according to protocols assessing staging, treatment outcome and complications.

Trials of antibody and chemotherapy have indicated that some patients may benefit from combined therapy. Trials combining Bevacizumab (anti-epidermal growth factor) and oxaliplatin/capectabine or oxaliplatin/fluorouracil/leucovorin have indicated enhanced efficacy of treatment in some, but not all types and stages of cancer tested. Trastuzumab (anti-HER2/neu) and paclitaxel has been approved for use in breast cancer for many years, has been found effective in anthracycline non-responders, and is gaining popularity as first line breast cancer therapy. Clinical trials with colorectal anti-cancer antibodies such as 17-1A (anti-Ep CAM of small cell carcinoma) and Cetuximab (anti-VEGF) and chemotherapeutic agents such as oxaliplatin or irinotecan have demonstrated improved outcomes with some, but not all types and stages of cancer.

As CD24 expression has been implicated in many types of cancer, the combination of efficacious specific anti-CD24 antibodies and additional therapeutic modalities, either as separate physical entities or attached, is an important clinical goal for treatment and prevention of cancer, particularly colorectal and pancreatic cancer.

SUMMARY OF THE INVENTION

According to some aspects of some embodiments, the present invention provides methods and compositions comprising anti-CD24 antibodies for treatment and prevention of cancer.

According to some aspects of some embodiments of the present invention there is provided a humanized monoclonal antibody which specifically binds an epitope of CD24 polypeptide.

According to some aspects of some embodiments of the present invention there is provided a pharmaceutical composition comprising as active ingredients an antibody which specifically binds an epitope of CD24 polypeptide and a chemotherapeutic agent and a pharmaceutically acceptable carrier.

According to some embodiments of the invention, the antibody has the amino acid sequence as set forth in SEQ ID NO: 21.

According to some embodiments of the invention, the epitope is an extracellular epitope.

According to some embodiments of the invention, the antibody is a humanized antibody.

According to further embodiments of the invention, the antibody is a monoclonal antibody.

According to further aspects of some embodiments of the present invention, the chemotherapeutic agent is attached to said antibody.

According to further aspects of some embodiments of the present invention there is provided a method of inhibiting growth of cancer cells, the method comprising contacting said cancer cells with therapeutic amount of an antibody which specifically binds an epitope of CD24 polypeptide and a chemotherapeutic agent.

According to further aspects of some embodiments of the present invention there is provided a method of treating or preventing growth of cancer cells in a subject in need thereof, the method comprising administering to said subject a therapeutic amount of an antibody which specifically binds an epitope of CD24 polypeptide and a chemotherapeutic agent.

According to some embodiments of the present invention the antibody is a monoclonal antibody.

According to some embodiments of the present invention the epitope of CD24 polypeptide is an extracellular epitope.

According to some embodiments of the present invention the antibody is a humanized monoclonal antibody.

According to some embodiments of the invention the antibody has the amino acid sequence as set forth in SEQ ID NO: 21.

According to some embodiments of the invention chemotherapeutic agent is attached to said antibody, and wherein said chemotherapeutic agent is exclusive of doxorubicin.

According to some embodiments of the invention the cancer is colorectal cancer or pancreatic cancer.

According to some embodiments of the invention subject is diagnosed with colorectal cancer or pancreatic cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
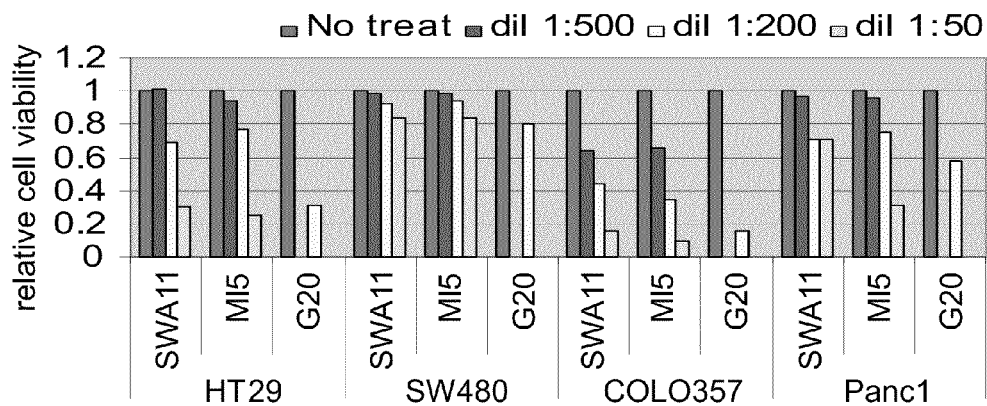
Figure 1B:
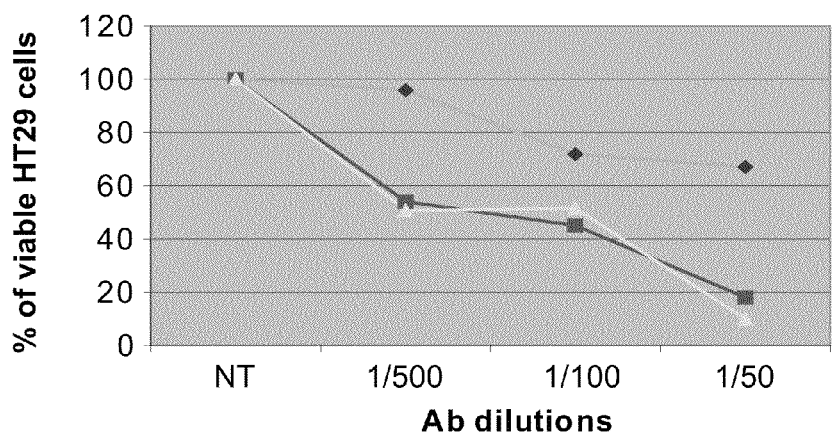
Figure 2:
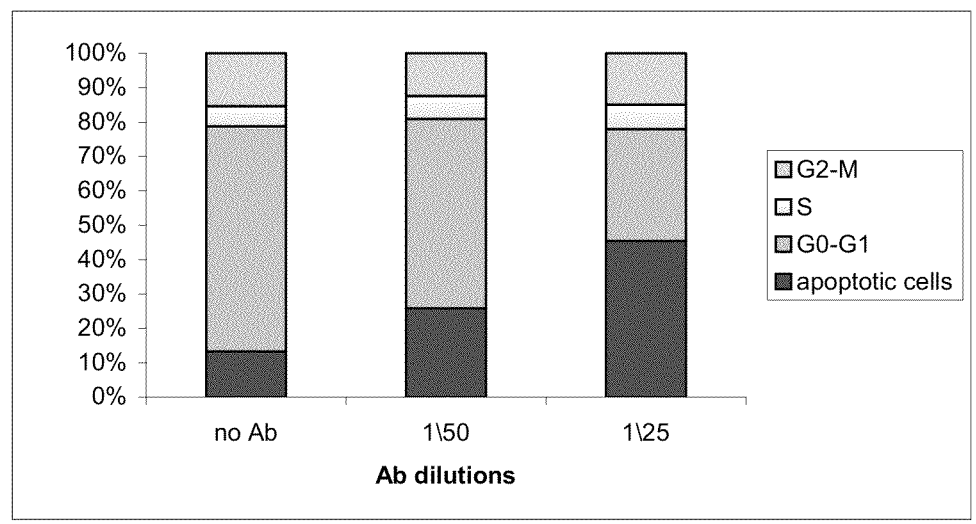
Figure 3:
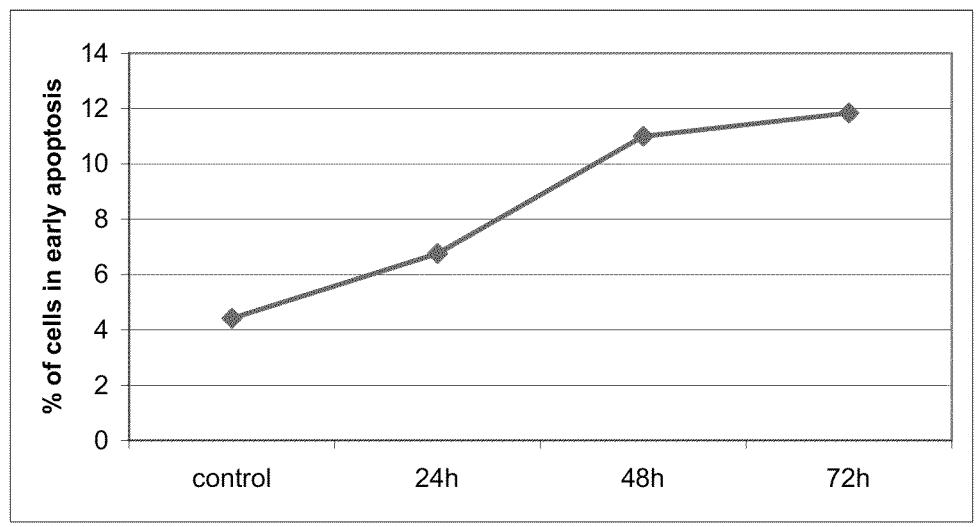
Figure 4:
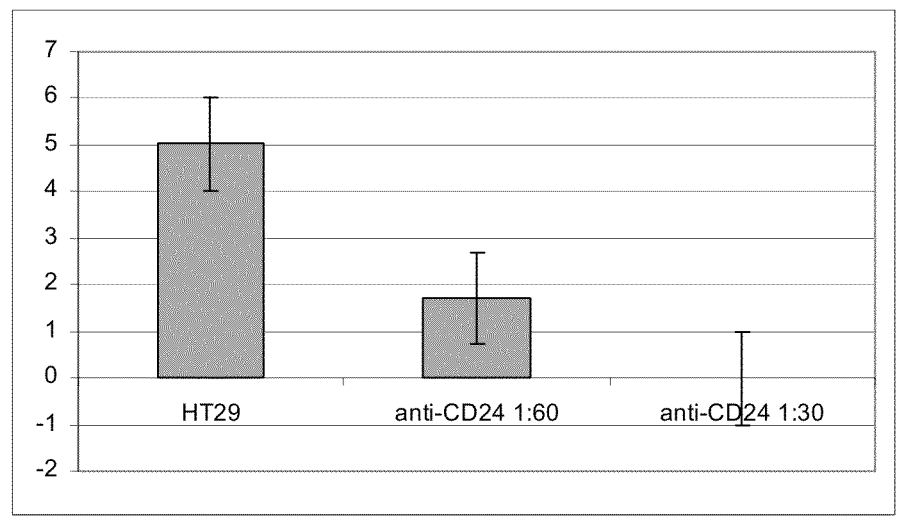
Figure 5A:
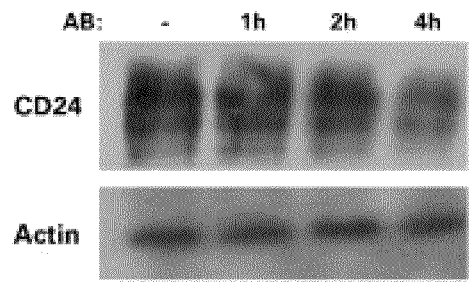
Figure 5B:
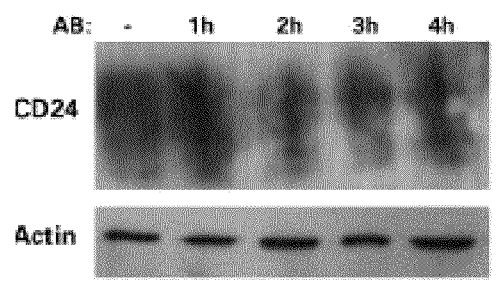
Figure 6:
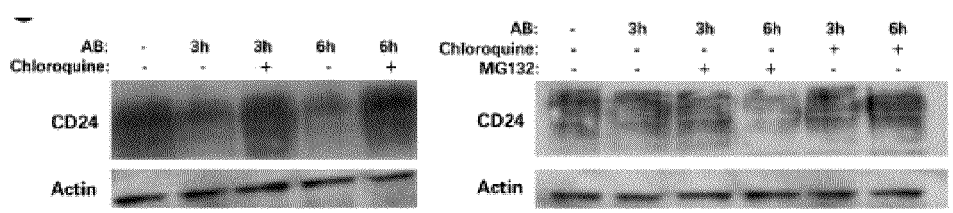
Figure 7:
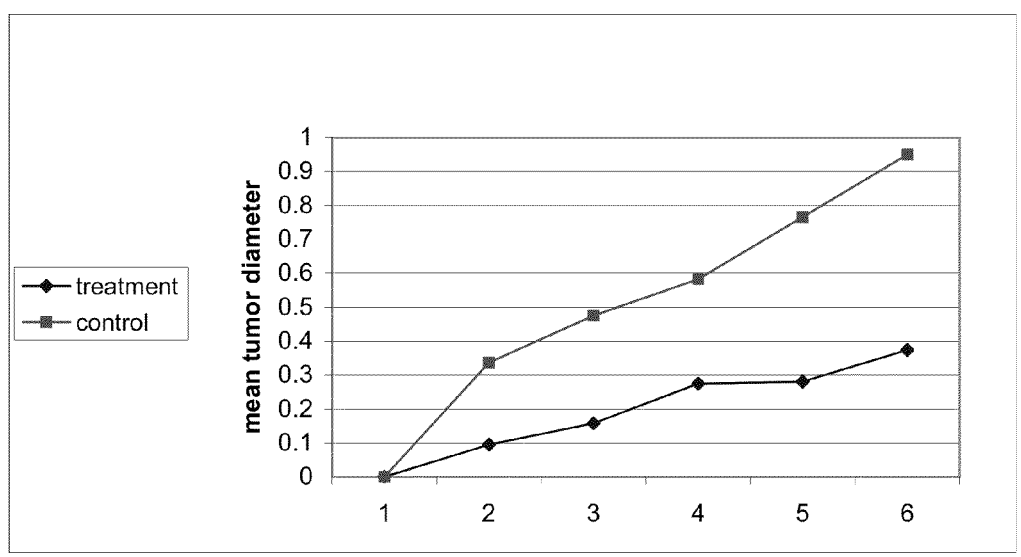
Figure 8A:
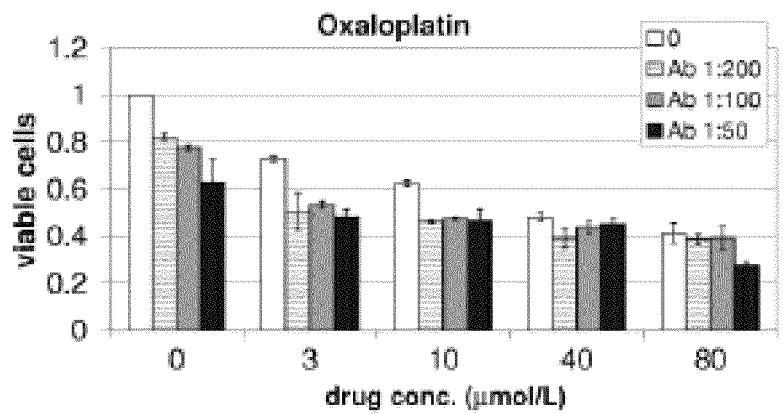
Figure 8B:
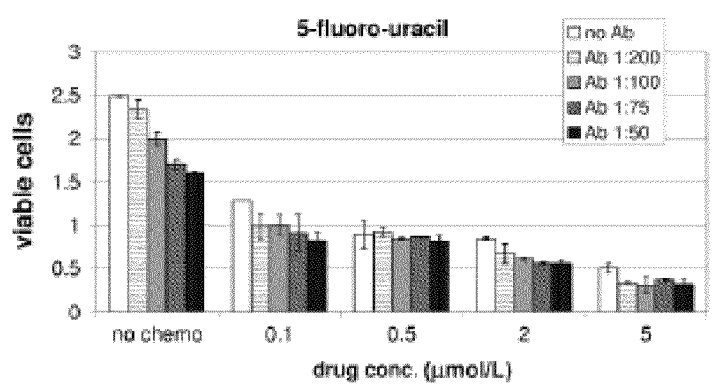
Figure 8C:
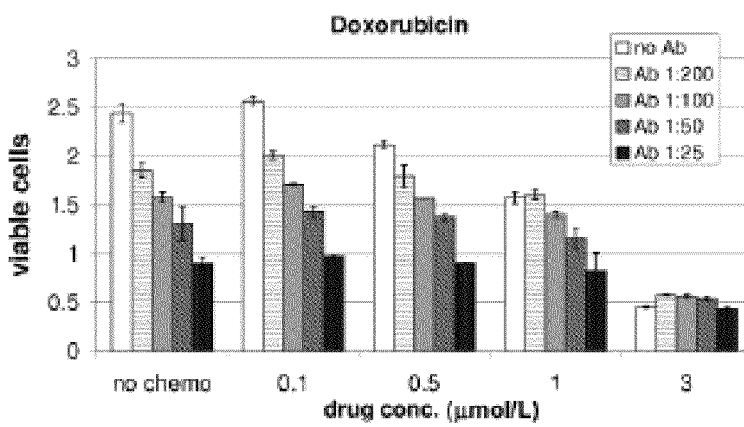
Figure 8D:
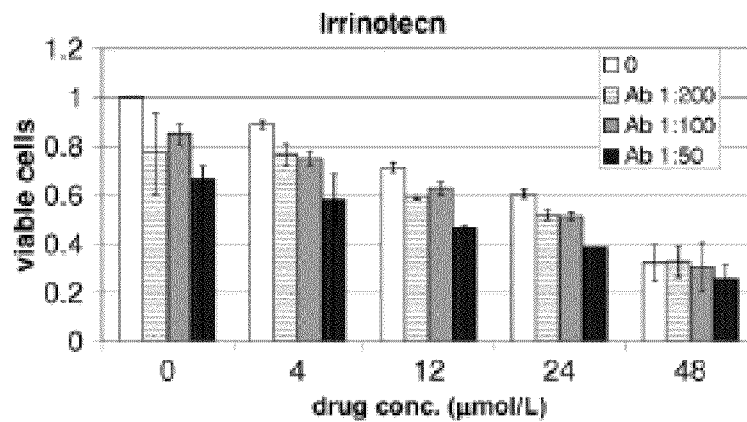
Figure 8E:
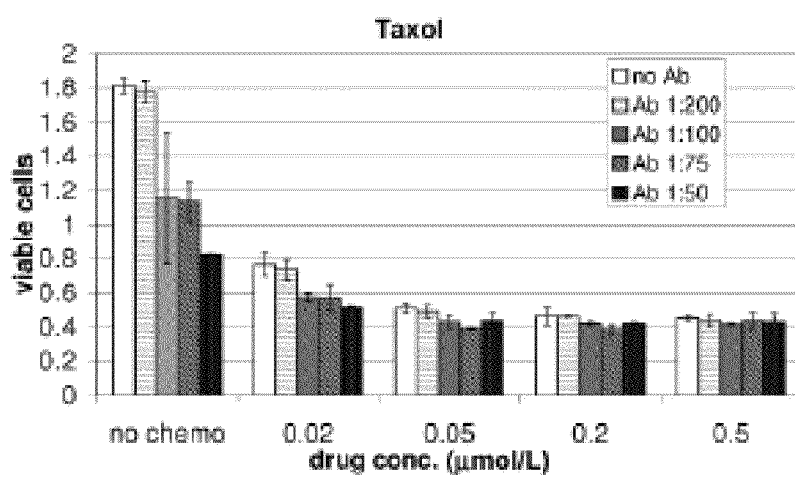

FIGS. 1A and 1B are graphs showing the inhibitory effect of monoclonal anti-CD24 antibodies on cancer cell viability in-vitro: In FIG. 1A HT-29, SW480, Colo357 and IEC18 cells, were seeded into 96-well plates ($2.5 \times 10^3$ cells/well). Twenty-four hours later, anti-CD24 monoclonal antibodies SWA11, ML-5 or C-20 were added at the indicated dilutions (aqua=1:50; yellow=1:200; red=500; no treatment=blue). Cell viability was measured 96 hours afterwards with methylene blue. In FIG. 1B, HT29, human colon cancer cells, were incubated with increasing doses of monoclonal anti-CD24 antibody SWA11. The indicated dilutions of Ab in the medium were refreshed every 48 hours for 48 hours (green plot), 96 hours (pink plot) and 144 hours (yellow plot). Note the clear growth inhibition under treatment with SWA11, in a time and dose dependent manner;

FIG. 2 is a bar graph showing the effect of monoclonal anti-CD24 antibody, at different dilutions, on cancer cell apoptosis and cell cycle, visualized by propidium iodide (PI). Cell cycle status is indicated as G2-M (tan); S-phase (Yellow); G0-G1 (Orange) or Apoptosis (Red). Note the striking increase in the number of apoptotic cells upon exposure to the monoclonal antiCD-24 antibody;

FIG. 3 is a graph showing the effect of monoclonal anti-CD24 antibody on cancer cell apoptosis, as measured by double staining with Annexin-V and PI. HT29 cells were seeded and exposed to 1:50 SWA11 anti-CD24 monoclonal antibody in 5% FBS growth medium for 24 to 72 hours. At the day of the experiment, cells were harvested and 2×10$^5$ cells of each plate were reacted with either anti-Annexin V fluorescent antibody, PI or both. The number of cells in early apoptosis phase (cells that bound Annexin-V but not yet absorbed the PI, which indicates late stage of cell death with fragmented cytoplasmic membrane) was assessed by FACS. Note the steady increase in apoptotic cells throughout the duration;

FIG. 4 is a bar graph showing the effect of exposure to anti-CD24 antibodies on cancer cell migration in a Transwell assay. 6×10$^4$ HT29 cells were seeded onto the upper chamber in 100 μl medium (5% fetal bovine serum); in duplicates, cells were suspended in medium that contains 1/30 and 1/60 dilutions of anti-CD24 antibody, SWA11 (as well as a control with no Ab addition). The lower chambers were filled with 600 μl of similar medium. 48 hours later, the cells that migrated through the pores to the lower side of the membrane were counted and compared to the number of cells seeded in a 24 wells plate as a control at the same time. Note the near total prevention of migration in SWA11-treated cells, while in the control wells (were cells were seeded on the plastic-ware itself) viable cells were still visible after 48 hours of the same treatment;

FIGS. 5A and 5B are photos showing immunodetection on Western blot of CD24 degradation in anti-CD24 mAb treated cancer cells. HT29 (FIG. 5A) and Colo357 (FIG. 5B) cells were exposed to monoclonal anti-CD24 antibody SWA11 for the indicated periods of time, cells harvested and protein extracted. 20 μg of cell proteins from each sample were separated by SDS-PAGE, blotted onto membrane and reacted with anti-CD24 (SWA11 mAb, CD24) or polyclonal anti-actin (1-19, Santa Cruz Biotechnology, Santa Cruz Calif.). Visualization was effected by anti-mouse and anti-goat (respectively) second antibodies. Note the degradation of CD24 apparent already at 2 hours treatment in both cell lines, with no effect on actin levels;

FIG. 6 is a photo showing the lysosomal mediation of CD24 degradation in HT29 cancer cells treated with anti-CD24 mAb. Following 2 hours exposure of HT29 cells to either the lysosomal inhibitor chloroquine (0.5 mM) or proteasomal inhibitor MG132 (0.1 mM), antibody treatment and immunodetection of CD24 and actin by Western blot were performed as in FIGS. 5A and 5B. Note the effect of lysosomal inhibitor chloroquine on CD24 degradation (left panel), and the lack of any effect of proteasomal inhibitor MG132 (right panel);

FIG. 7 is a graph showing the inhibition of tumor growth in-vivo by intravenous administration of anti-CD24 mAb. 7×10$^6$ HT29 cells suspended in 0.15 ml PBS per injection were injected into the flanks of athymic (nude) mice, producing subcutaneous tumors visible 7-10 days following injection. Starting one day after the injection of the cells, each mouse of the antibody group (solid squares, ■) was injected twice-weekly in the tail vein with approximately 30 μg (150 μl) of monoclonal anti CD24 antibodies (ML-5) (n=4 mice, X 2 tumors per mouse, equals 8 tumors). A control group of tumor bearing mice received no antibody (n=6 mice, X 2 tumors per mouse, equals 12 tumors) (solid diamonds, ♦). Each tumor diameter was measured twice weekly using a micrometer caliper, and tumor volumes were calculated as: $4/3\pi r^3$, as described. Note the significant and progressive reduction in tumor growth of anti-CD24 mAb treated mice;

FIGS. 8A-8E are graphs showing enhanced inhibition of cancer cell growth by combined anti-CD24 mAb and chemotherapeutic treatment. HT29 cells grown as described above were treated with SWA11 anti-CD24 antibodies for 72 hours at the indicated concentrations, in combination with the various concentrations of five accepted chemotherapeutic agents: Oxaloplatin (FIG. 8A), 5-fluorouracil (FIG. 8B), Doxorubicin (FIG. 8C), Irrinotecan (FIG. 8D) and Palitaxol (FIG. 8E). Experiments were performed in duplicates or repeated twice. The Y axes stand for cell viability quantified via methylene-blue assay. Note the significant reduction in HT29 cell growth in combined treatment with some of the agents (at least 50% with Doxorubicin and Irrinotecan).

DESCRIPTION OF EMBODIMENTS OF THE INVENTION

The present invention is of anti-CD24 antibodies and adjuvant combinations thereof with chemotherapeutic agents or toxins, which can be used to inhibit growth of CD24-expressing cancer cells and prevent and treat cancer.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

An evolving body of literature has linked CD24 with rapid cancer cell growth in numerous types of cancer (breast cancer, colorectal cancer, small cell lung cancer, bladder cancer, pancreatic cancer, inter alia), and CD24 has been proposed as a diagnostic marker in these diseases. However, published studies in this field appear to be divided as to the role of CD24. On the one hand, CD24 was suggested in some studies to contribute to malignant transformation as a peptidoglycan carrying the appropriate glycans (the sialylLe$^x$ residue) which allows it to bind P-selectin.

Other studies suggest that CD24 also plays a role in intracellular changes, initiated, probably, by evoking an intracellular signal transduction though as yet defined pathways but which might include the Ras, MAPK or BCL2 pathways. It should also be noted that CD24 expression was correlated with changes in cell growth in a monolayer culture with the absence of selectins and not only in clinical correlations.

While reducing the present invention to practice, the inventors have shown that specific anti-CD24 antibodies can inhibit cell growth in CD24-expressing cells, and are effective in reducing tumor growth in-vivo (see Examples I and II). Further, the inventors have shown that administration of anti-CD24 antibodies in combination with chemotherapeutic agents or cytotoxins greatly enhances the growth-inhibiting effect of both treatments on CD24-expressing cancer cells.

Thus, according to one aspect of the present invention there is provided a composition comprising as active ingredients an antibody which specifically binds an epitope of CD24 polypeptide and a chemotherapeutic or cytotoxic agent.

As used herein "a CD24 polypeptide" refers to a glycosylphosphatidylinositol (GPI)-anchored cell surface protein having 31 amino acids with 16 potential O- and N-glycosylation sites (in the human). Human CD24 is encoded by the CD24 gene, and is first expressed as an 80 amino acid precursor (Accession No. ACI46150).

As used herein, the term "epitope" refers to a portion or portions of an immunogenic compound which elicits an immune response such as antibody production, and capable of binding with the resultant antibody. Exemplary epitopes of CD 24 are the sialic and the LAP (leucine-alanine-proline) epitopes.

It will be appreciated that cellular and cell surface proteins have epitopes which correspond to regions of the antigen within the cells, extracellular portions of the antigen, and trans-membrane portions of the antigen. CD24 polyprotein is a cell surface protein lacking a trans-membrane domain. Thus, according to one embodiment of the present invention, the CD24 epitope is an extracellular epitope.

As used herein, in the context of the invention, the term "binding" relates to the reversible, non-covalent association between an antibody, or an antigen binding portion of an antibody, and an antigen, or an antibody-binding epitope thereof. Such a relationship can be described in terms of a strong binding capacity of the antibody for the epitope, in which case the Ab-antigen binding takes place with high affinity, or in terms of weak or weaker binding capacity of the antibody for the epitope, or vice versa. In weaker binding capacity, the Ab-antigen binding occurs with less affinity, and is more susceptible to interference by other antigenic epitopes or reaction conditions.

As used herein, the term "antibody" refers to a substantially intact antibody molecule.

As used herein, the phrase "antibody fragment" refers to a functional fragment of an antibody (such as Fab, F(ab')2, Fv or single domain molecules such as VH and VL) that is capable of binding to an epitope of an antigen. For example, in one embodiment, the fragment is the heavy chain $V_H$ of the anti-CD24 monoclonal antibody SWA11, as set forth in SEQ ID NO: 12, or the light chain $V_L$ of the anti-CD24 monoclonal antibody SWAM as set forth in SEQ ID NO: 14.

Suitable antibody fragments for practicing the present invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(v) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vi) Single domain antibodies are composed of a single VH or VL domains which exhibit sufficient affinity to the antigen.

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120). Anti-CD24 antibodies, both polyclonal and monoclonal, suitable for use in the methods and compositions of the present invention are commercially available, for example, from Santa Cruz Biotechnology (Santa Cruz, Calif.), AbDSerotec (Kidlington, UK) and Life Span BioSciences, Inc (Seattle Wash.).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumine (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in *E. coli* or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove the variable domains can be linked to generate a single chain Fv by an intermolecular disulfide bond, or alternately, such chains may be cross-linked by chemicals such as glutaraldehyde.

Preferably, the Fv is a single chain Fv.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as $E.\ coli$. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Isolated complementarity determining region peptides can be obtained by constructing genes encoding the complementarity determining region of an antibody of interest. Such genes may be prepared, for example, by RT-PCR of mRNA of an antibody-producing cell. Ample guidance for practicing such methods is provided in the literature of the art (for example, refer to Larrick and Fry, 1991. Methods 2:106-10).

It will be appreciated that for human therapy or diagnostics, humanized antibodies are preferably used. Humanized forms of non human (e.g., murine) antibodies are genetically engineered chimeric antibodies or antibody fragments having—preferably minimal—portions derived from non human antibodies. Humanized antibodies include antibodies in which complementarity determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies. In one embodiment of the present invention, the anti-CD24 antibody is a humanized anti-SWA11 antibody, wherein the scFv portion (SEQ ID NO: 21) is produced as described herein.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

It will be appreciated that targeting of particular compartment within the cell can be achieved using intracellular antibodies (also known as "intrabodies"). These are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker [e.g., $(Gly_4Ser)_3$ and expressed as a single chain molecule. To inhibit marker activity in a cell, the expression vector encoding the intracellular antibody is introduced into the cell by standard transfection methods, as discussed hereinbefore. In one embodiment of the present invention, the $V_H$ and $V_L$ are attached via the flexible linker G G S G G G G S G G G G S (SEQ ID NO: 20).

Once antibodies are obtained, they may be tested for activity, for example via ELISA.

As used herein, the terms "combination therapy", "adjuvant therapy" and "neoadjuvant therapy" are used interchangeably to indicate the intentional combination of antiCD24 antibody treatment with at least one additional treatment.

To facilitate targeted inhibition of growth of cancer cells, the anti-CD24 antibodies of the present invention can be used in combination with chemotherapeutic agents. Examples of chemotherapeutic agents that can be used in combination with the antiCD24 antibodies of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Oxaliplatin; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). In specific embodiments, the anti-CD24 antibody is administered in combination with a chemotherapeutic agent exclusive of Doxorubicin. In further specific embodiments, the chemotherapeutic agent is Oxaloplatin or 5-fluorouracil, Irrinotecan or Palitaxol.

Combination or adjuvant therapy employing a "cocktail" of chemotherapeutic agents, or employing a regimen of different chemotherapeutic agents at different times during the treatment is common in anti-cancer medicine. For example, anthracycline agents are often paired with, or followed by metabolic agents in treatment of breast cancer. Thus, it will be appreciated that the antiCD24 antibody of the present invention can be used in combination with more than one chemotherapeutic agent at a time, or with a variety of chemotherapeutic agents over the course of treatment for the same cancerous condition. Further, a regimen of antiCD24 antibody combined with chemotherapy agents can be employed in conjunction with, and in addition to other anti-cancer therapies such as surgery, radiation, nutritional therapy and the like.

The anti-CD24 antibodies of the present invention can be combined with chemotherapeutic agents in a variety of forms. The combination can be an admixture, a chemical compound comprising the agents and the antiCD24 antibody linked by covalent or ionic chemical bonding, a chemically synthesized or recombinant fusion protein, etc. According to one embodiment of the present invention, the anti-CD24 antibodies are co-administered with the chemotherapeutic agents via common methods of administration, such as intravenous, subcutaneous, intraperitoneal, oral, etc. administration.

For example by using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bisazido compounds (such as bis-(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a 5-FU peptide conjugate can be generated as described by Semko (1996) Peptides Abst. $24^{th}$ Symp. Eur. Pept. Soc. P26. A ricin-peptide conjugate can be prepared as described in Vitetta et al., Science, 238: 1098 (1987). 1-isothiocyanatobenzyl-3-methyldiethylene triaminepentaacetic acid (MX-DTPA) is an exemplary chelating agent for conjugation of radionucleotide to the antibody (see WO94/11026).

The anti-CD24 antibodies of the present invention can be used in combination with radioisotopes for inhibiting growth of cancer cells. Examples of radio-isotopes include cytotoxic radio-isotopes such as β radiation emitters, γ emitters and α-radiation emitting materials. Examples of β radiation emitters which are useful as cytotoxic agents, include isotopes such as scandium-46, scandium-47, scandium-48, copper-67, gallium-72, gallium-73, yttrium-90, ruthenium-97, palladium-100, rhodium-101, palladium-109, samarium-153, rhenium-186, rhenium-188, rhenium-189, gold-198, radium-212 and lead-212. The most useful γ emitters are iodine-131 and indium-m 114. Other radio-isotope useful with the invention include α-radiation emitting materials such as bismuth-212, bismuth-213, and At-211 as well as positron emitters such as gallium-68 and zirconium-89.

As is mentioned hereinabove, one specific use for the antiCD24 antibodies and combinations of the present invention is prevention or treatment of cancer.

Thus, according to another aspect of the present invention, there is provided a method of treating or preventing growth of cancer cells in a subject. Preferred individual subjects according to the present invention are mammals such as canines, felines, ovines, porcines, equines, bovines, humans and the like.

The term "treating" refers to alleviating or diminishing a symptom associated with cancer. In one embodiment of the present invention, treating cures, e.g., substantially eliminates, the symptoms associated with the cancer. In another embodiment, the treating results in inhibition of growth of cancer cells, e.g. reduction in size of a cancerous tumor, arrest of tumor development or reduction in metastatic spread of a primary or secondary cancer.

According to yet another embodiment of the present invention, there is provided a method for inhibiting the growth or development of cancer cells. Such growth inhibition can be performed, for example, as ex-vivo treatment of cancerous cells before their return to the subject's body.

As used herein, the phrase "cancer" refers to diseases associated with the proliferation of mammalian cells. As used herein, the term "CD24-expressing cancer cell" refers to a cell expressing the CD24 surface polypeptide recognized by the CD24 antibodies of the invention.

Cancers include, but are not limited to, acute or chronic myelogenous leukemia, mixed lineage leukemia, breast cancer, colon cancer, prostate cancer, lung cancer and T-cell leukemia, B-lineage acute lymphoblastic leukemia, chronic lymphocytic leukemia, B-lineage lymphoma, blast crisis of chronic myelocytic leukemia, hairy cell leukemia, AIDS lymphoma, EBV-lymphoma, brain tumors, neuroblastoma, osteosarcoma, soft tissue sarcoma, ovarian cancer, testicular cancer or melanoma. Colorectal cancer and pancreatic cancer cells have been shown to over-express CD24 during oncogenesis. Thus, in one specific embodiment of the present invention, the cancer and/or cancer cells are colorectal cancer or pancreatic cancer cells.

The method includes providing to the subject a therapeutically effective amount of the antibody or antibody in combination with a chemotherapeutic agent of the present invention. The antibody or combination can be provided using any one of a variety of delivery methods. Delivery methods and suitable formulations are described hereinbelow with respect to pharmaceutical compositions.

The antibody or antibody in combination with a chemotherapeutic agent of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It is expected that during the life of a patent maturing from this application many relevant methods for downregulating bee pathogen proteins will be developed and the scope of the term "downregulating bee pathogen protein" or "downregulating bee pathogen polypeptide" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat.

Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

Materials and Experimental Methods

Cell Culture

The human colorectal (HT29) and pancreatic (Colo357) cancer cell lines were obtained from the American Type Culture Collection (Manassas, Va.), cultured in Dulbecco's modified Eagle medium (Sigma, Israel) containing 5%-10% fetal bovine serum (Biological Industries, Beit Haemek, Israel), 1% penicillin, and 1% streptomycin (complete medium) at 37° C. in an atmosphere of 95% oxygen and 5% $CO_2$.

Protein Extraction and Western Blotting

Exponentially growing cells were harvested and protein concentrations were determined using the Bio-Rad protein assay kit (Bio-Rad, Hercules, Calif.). For analysis, 20 μg from each lysate loaded on SDS-PAGE and the proteins were transferred to hybond-C extra nitrocellulose membranes (Amersham Life Science, Buckinghamshire, United Kingdom). Membranes were blocked with buffer containing 5% low-fat milk and 0.05% Tween 20 in PBS for 1 hour, incubated with primary antibodies for 1 hour, with peroxidase-conjugated secondary antibodies, and developed with a Supersignal West Pico chemiluminescent substrate (Pierce, Rockford, Ill.). As primary antibodies SWA11 (anti-CD24) and polyclonal anti-actin (1-19; Santa Cruz Biotechnology, CA) were used. Anti-mouse and anti-goat (Jackson Laboratories, Bar Harbor, Me.) were employed as secondary antibodies, respectively.

Protein analysis following therapy under chloroquine induced inhibition of lysosome, cells ($7\times10^5$/well) were plated onto 6 wells plate and treated on the morrow. Chloroquine was added two hours before treatment. SWA-11 was added to the medium at 1:40 dilution. Cells were removed from the plate with a rubber policeman at the end of the treatment.

SWA11-Humanization of SWA11 Anti-CD24 Monoclonal Antibody

The N-terminal amino acid sequence of the SWA11 mAb, heavy (SEQ ID NO: 5) and light chains (SEQ ID NO: 6), were sequenced by Edman degradation protein sequencing:

$V_H$-DVQLQESGPDLVKPS     (SEQ ID NO: 1)

$V_L$-DIVMSQSPSSLNVSVGEKVTMRC  (SEQ ID NO: 2)

Then total cellular RNA was prepared from SWA11 hybridoma cells and cDNA synthesis was performed. SWA11 was cloned from the hybridoma RNA by RT-PCR followed by PCR amplification using the C-region primers, Mu-IgG2a-CH1-Rev (SEQ ID NO: 3) and Mu-C-KAPPA-Rev (SEQ ID NO: 4), and the V primers, $V_H$-for (SEQ ID NO: 5) and $V_L$-for (SEQ ID NO: 6). Sequencing of the resulting RT-PCR products allowed us to identify the exact C-termini of the $V_H$ and $V_K$ domains. The sequences for these regions are designated SEQ ID NO: 7 ($V_H$ domain) and SEQ ID NO: 8 ($V_L$ domain).

The heavy chain expression vector pMAZ-IgH was constructed on the backbone of pCMV/myc/ER/Neo (Invitrogen, USA). The human gamma 1 constant heavy chain region (CH1-CH3) was recovered by PCR from human lymphoid cDNA.

Murine SWA11 VH domain was amplified using primers SWA11VH-NheI-REV (SEQ ID NO: 9) and SWA11VH-BssHII-FOR (SEQ ID NO: 10) and introduced into the heavy chain vector as a BssHII/NheI fragment. The light chain expression vector pMAZ-IgL was constructed on the backbone of pcDNA3.1/Hygro (Invitrogen, USA). Murine SWA11 light chain was amplified using primers SWA11VL-BssHII-FOR (SEQ ID NO: 10) and SWA11VL-BsiWI-REV (SEQ ID NO: 11) and introduced into the light chain vector as BssHII/BsiWI fragment.

The amino acid sequence for the resulting IgH is SEQ ID NO: 12, encoded by DNA sequence as set forth in SEQ ID NO: 13. The sequence for the resulting IgL is designated SEQ ID NO: 14, encoded by DNA sequence SEQ ID NO: 15.

The scFv was constructed into the pCC16 vector in two PCR reactions. For the amplification of the VH regions we used primers SWA11VH-NcoI-FOR (SEQ ID NO: 16) and SWA11VH-BlpI-REV (SEQ ID NO: 17) and for the amplification of the VL region we used primers SWA11VL-EcoRV-FOR (SEQ ID NO: 18) and SWA11VL-NotI-REV (SEQ ID NO: 19). The VH domain and the VL domain are linked together by a flexible linker (yellow) (SEQ ID NO: 20) to produce the complete humanized SWA11 scFv amino acid sequence (SEQ ID NO: 21), encoded by the DNA sequence as set forth in SEQ ID NO: 22.

The combined scFvs PCR products were digested and cloned into the pMALc-NN vector via the NcoI and NotI, restriction sites for expression as MBP-scFvs.

Construction of scFv-PE38 Targeted Immunotoxin

The immunoconjugate was constructed by non-chemical linking of anti-CD24 mAb (SWA11 IgG2a) to a fusion protein, ZZ-PE38, in which the IgG-Fc binding protein ZZ was fused to the N-terminus of the *Pseudomonas* exotoxin derivate; PE38.

In order to construct the scFv-PE38 immunotoxin the scFv fragment was excised from the pCC16 vector by a PCR reaction using the primers SWA11VH-NdeI-FOR(SEQ ID NO: 23) and SWA11VL-HinDIII-REV (SEQ ID NO: 24) and subcloned into the pRB98 vector.

Cytotoxic activity was assayed in-vitro in CD24-expressing (HT29, Colo320 and Colo357) and CD24-non-expressing (HCT116) CRC and PC cells.

Reverse-Transcriptase PCR (RT-PCR)

Total RNA was prepared from the cell lines, using Tri Reagent (Molecular Research Center, Cincinnati. Ohio, USA). RT-PCR reaction was performed, with 50 ng, on PTC-100 programMABle thermal controller (MJ Research Inc, USA). Primers were designed as follows:

Glyceraldehyde-3-phosphate dehydrogenase (GAPDH-housekeeping gene): Forward, 5'-GGAGATTGTTGCCAT-CAACG-3' (SEQ ID NO: 25); Reverse, 5'-TTGGTGGTG CAGGATGCATT-3'(SEQ ID NO: 26).

CD24: Forward, 5'-GGCACTGCTCCTACCCACGCAG-3' (SEQ ID NO: 27); Reverse, 5'-GCCACATTGGAATTC- CAGACGCC-3' (SEQ ID NO: 28). The PCR products were separated in 2% agarose/GelStar gel and visualized under UV light.

Cell Proliferation Rate

Cells were plated at a density of $5\times10^4$ per well in 12 well plates, using 1 ml of complete medium (DMEM/5% FBS) or medium deficient with bovine serum (0.5% FBS), as indicated. Starting on the morrow, two wells for each cell line were counted every other day using a Coulter particle counter (Coulter Electronics Luton, England). Media were replenished twice weekly during 21 days. Flow cytometry analysis for cells stained with propidium iodide for cell cycle parameters was performed as previously described (Runz S, et al. Biochem Biophys Res Commun, 2008; 365: 35-41).

Cell Migration Assay

A three-dimensional cell migration assay was performed with the Transwell system (Corning, N.Y.), which allows cells to migrate through an 8-μm pore size polycarbonate membrane. Complete medium was first added to the 24-well plate well (the lower chamber of Transwell), and then to the Transwell insert (the upper chamber of Transwell) and prepared in the incubator for 3-5 hours. Cells were trypsinized, washed, and resuspended in DMEM medium containing 5% fetal bovine serum ($6\times10^5$ cells/ml). The cell suspension (1000) was plated onto the upper chamber (insert) of the Transwell. The lower chamber was filled with 6000 of the same medium. After incubation for 48 h at 37° C., the cells were fixed for 10 min in 4% paraformaldehyde, perforated with 0.01% Triton (Sigma) for 5 min and stained for 5 min with crystal violet. The filters were then rinsed thoroughly in distilled water and the non-migrating cells were carefully removed from the upper surface of the Transwell with a wet cotton swab. The wells were counted and the number of trans-migrated cells was assessed by color quantification using the TINA 2.0 software.

Xenograft Model in Mice for Measuring In-Vivo Tumor Development

Athymic "nude" mice were housed in sterile cages and were handled with aseptic precautions and supplemented with ad libitum nutrition. Exponentially growing cells were harvested with brief treatment of 0.25% Trypsin-EDTA solution, and resuspended at a final concentration of 5 to $7.5\times10^6$ cells per 0.15 ml PBS per injection as indicated. The cells were injected subcutaneously into two sites on the back of the mice. The mice were weighed and the tumor growth was measured twice a week; tumor volumes were calculated as $4\pi ab^2/3$. At the end of the experiment, mice were sacrificed by cervical dislocation following anesthesia and examined for the presence of further metastases. Tumors were excised, weighed and the volume was measured with calipers. Each assay was repeated at least twice. For measuring tumorigenicity of the formed clones, four mice (eight tumors) served for each cell line. For testing the therapeutic potential of the anti-CD24 antibodies, in each experiment 10 mice were injected with HT29 cells (20 tumors) and randomized for a control (saline) or AB group. Therapy was injected twice weekly, in a volume of 0.15 ml, or approximately 0.3 mg Ab (representing approximately 15 mg/Kg body weight).

Growth Inhibition Induced by Monoclonal Antibodies to CD24

The killing effect of the anti-CD24 antibodies and the chemotherapies was assessed, in-vitro, using a methylene-blue assay: $2.5\times10^3$ cells/well were plated onto 96-well in 0.2 ml complete medium. On the morrow the media were refreshed with the addition of the indicated reagents, held in incubation for 72 hours. The cells were washed with PBS and then fixed with a 0.2 mL 4% formaldehyde solution for 2 hours at room temperature. The cells were then washed with PBS, incubated with 0.15 mL ribonuclease A (3 μg/mL) for 30 minutes at room temperature, equilibrated with 0.2 mL sodium borate (0.1M, pH 8.5), and stained with 0.2 mL methylene blue (0.5%) for 10 minutes at room temperature. Finally, the cells were thoroughly washed with tap water and cell-bound dye was eluted with 0.2 mL HCl (0.1M). Color intensity was read in an enzyme-linked immunosorbent assay plate reader at 595 nm. SWA11 served as the anti-CD24 antibody. Paclitaxel, Doxorubicin, and 5-florouracil were obtained from Sigma (Rehovot, Israel); Oxaliplatin and Irrinotecan were obtained from Aventis Pharma (Dagenham, UK).

Results

Example I

Anti-CD24 Antibodies Inhibit Cancer Cell Growth

Antibodies to CD24 Mediate Inhibition of Cell Proliferation.

In order to determine whether CD24 can be suitable for treatment of colorectal cancer (CRC) and pancreatic cancer, well-known cell lines representing models of colorectal and pancreatic cancer were exposed to anti-CD24 monoclonal antibodies, and the effect on cell viability and proliferation was measured.

Anti-CD24 mAb induces apoptosis in CD24 expressing (HT 29, Colo357) but not in non-expressing (SW-480 and PANC-1) human cancer cells (FIGS. 1A and 1B). Similar growth inhibition, in these four cell lines, was observed when the cells were exposed to two additional monoclonal antibodies for different epitopes: ML-5 and C-20 (FIG. 1A). Note that the growth of HT29 and Colo357 cells was inhibited in up to 90%. When time course and dose-response of the effect of anti-CD24 monoclonal Ab SWA11 on HT29 cells was assessed, results showed that exposure to SWA11 mAb resulted in a time- and dose-dependent loss of cell viability (FIG. 1B).

Apoptosis Induction is a Factor in Growth Inhibition of Cancer Cells by Anti-CD24 mAb.

Using flow cytometry analysis for cancer cells pre-stained with propidium iodide (PI) we determined the changes in cell cycle distribution that result from treatment with anti-CD24 monoclonal antibody. HT29 cells that strongly express CD24 were seeded equally ($7\times10^6$ cells per 10 cm plate) in 5% FBS medium. On the following day, the growth medium was changed to medium that contained no antibodies, or medium containing 1:50 or 1:25 SWA11 anti-CD24 monoclonal antibody (FIG. 2). 48 hours later cells were harvested, fixated in ethanol (1 h at 4° C.), treated with RNAse (30 min at 37° C.) and stained with PI for (15 min in dark-room) (FIG. 2).

FIG. 2 shows that exposure to both 1:25 and 1:50 dilutions of SWA11 resulted in a significant dose-related increase in the proportion of apoptotic cells (red bars) in comparison with cells in the G0/G1 phase (orange bars).

Annexin-V staining is another measure of apoptosis in cells. In order to further demonstrate the increase in levels of apoptosis of HT29 cells when exposed to anti-CD24 monoclonal Ab, Annexin-V and PI double staining was used. HT29 cells were seeded and exposed to 1:50 SWA11 anti-CD24 monoclonal antibody in 5% FBS growth medium for 24 to 72 hours. Cells were then reacted with either anti-Annexin V fluorescent antibody, PI or both. The number of cells in early apoptosis phase (cells that bound Annexin-V but do not yet take up PI, which indicates late stage of cell death with fragmented cytoplasmic membrane) was assessed by FACS (FIG. 3). Clearly, exposure of the HT29 cells to anti-CD24 monoclonal Ab results in a significant increase in levels of apoptosis.

Anti-CD24 Antibodies Inhibit Migration in HT29 Cells.

Cell migration is a critical function of cancerous and, particularly, metastatic cells. In order to assess the effect of anti-CD24 antibodies on this aspect of cancer development, migration was assayed using transwell plates, 0.8 μm pore size (Corning, N.Y.). Cells exposed to monoclonal anti-CD24 antibody (SWA11) showed almost no migration (transition through the membrane). In the control wells (where cells were seeded directly on the wells) viable cells were still visible after 48 hours culture under identical conditions.

Anti-CD24 Antibodies Inhibit Growth of Cancer Cells Via Lysosome-Related Proteolysis.

In order to assess whether CD24 proteolysis is involved in the inhibition of CD24-expressing cancer cell growth by anti-CD24 antibodies, protein levels of CD24 and housekeeping gene product actin in mAb-treated and control cells were analyzed by SDS-PAGE and Western blotting with specific antibodies.

HT29 (FIG. 5A) and Colo357 (FIG. 5B) cells demonstrated significant degradation of CD24 protein within a few hours of exposure to anti-CD24 mAb SWAM while actin levels remained constant, indicating specific CD24 proteolysis. No change in the transcription level of CD24 was seen under the same conditions (data not shown).

In order to determine the role of lysosomal degradation of CD24 in the growth inhibitory effect of anti-CD24 mAb, cells were exposed to 0.5 mM chloroquine (lysosomal inhibitor) or 0.1 mM MG132, prior to the anti-CD24 mAb treatment. PAGE and Western blot analysis of CD24 compared to actin levels in the cells up to 6 hours later indicated that chloroquine prevented the decrease in CD24 protein level that accompanied the growth inhibition induced by the anti-CD24 mAb (FIG. 6), while exposure to MG132 had no effect on CD24 degradtion. Taken together, these results suggest that CD24 degradation is lysosomally mediated.

Thus, extensive assessment of the effects of monoclonal anti-CD24 antibodies on growth, apoptosis and migration of cancer cells uncovered significant inhibition of cancer cell development, without affecting non-CD24 expressing cells indicating promising therapeutic potential of anti-CD24 antibodies.

Example II

Antibodies to CD24 Inhibit In-Vivo Tumor Formation

The effect of anti-CD24 monoclonal antibodies on tumors in-vivo was assessed in the subcutaneous tumor model. Subcutaneous tumors were formed in nude mice as described herein.

The results shown in FIG. 7 clearly show the ability of anti-CD24 monoclonal antibody to prevent tumor growth in-vivo as well as in-vitro, as shown hereinabove.

Similar results were accepted in a smaller experiment where two mice bearing tumors induced similarly by HT29 cells, were treated with intra-peritoneal administration of anti-CD24 mAb, ML-5. This indicates that the in-vivo anti-cancer effect of anti-CD24 mAbs is not limited to a single route of administration or formulation.

Example III

Enhanced Tumor Cell Death with Combined Anti-CD24 Monoclonal Antibody and Chemotherapy Treatment There is a great need for reducing effective dosage of chemotherapeutic agents delivered systemically in anti-cancer treatment. In order to assess the efficacy of combined anti-CD24 and chemotherapy treatment on cancer growth, HT29 cells were treated simultaneously with varying concentrations of anti-CD24 monoclonal Ab SWA11 and incremental doses of the leading chemotherapeutic agents Oxaloplatin (FIG. 8A), 5-florouracil (FIG. 8B), Doxorubicin (FIG. 8C), Irrinotecan (FIG. 8D) and Paclitaxel (FIG. 8E), and viability of the cells assayed by methylene blue exclusion (FIGS. 8A-8E). Anti-CD24 monoclonal antibody therapy enhanced the cytotoxic effect of all five chemotherapeutic agents. The increased efficiency varied according to the therapeutic agent in use, but in some combinations, the addition of the mAb, already at comparatively low dilutions (1:100 of the mAb distributed in the medium) allowed to decrease the dose of the chemotherapeutic agent in more than 50% (e.g. Doxorubicin and Irrinotecan).

Taken together, these results indicate that combination of the specific ant-cancer effects of anti-CD24 antibody treatment with the more general action of toxic chemotherapeutic agents can enhance therapeutic efficacy in anti-cancer treatment.

Example IV

Targeting Toxins to Cancer Cells with Anti-CD24 Monoclonal Antibody: Immunotoxins In order to explore the potential of anti-CD24 in antibody-targeted cancer therapy, a novel recombinant immunoconjugate complexed to a cytotoxic-agent was developed.

A SWA11-pseudomonas exotoxin immunoconjugate was constructed by non-chemical linking of a humanized anti-CD24 mAb (SWA11 IgG2a) to a fusion protein, ZZ-PE38 (the N-terminus of the *Pseudomonas* exotoxin derivate; PE38). Cytotoxicity was assayed in CD24-expressing (HT29, Colo320 and Colo357) and non-expressing (HCT116) CRC and PC cells.

Results of comparison of cell viability following exposure of the cancer cells to the SWA11-ZZ-PE38 immunoconjugate show that SWA11-ZZ-PE38 has improved cytotoxity compared to non-armed SWA11 anti-CD24 mAb. Importantly, SWA11-ZZ-PE38 also exhibited significant improved binding affinity and cytotoxity ($LD_{50}$=32 ng/ml) towards CD24-positive cells as compared to binding affinity and toxicity towards non-expressing cells ($LD_{50}$>>>>10,000 ng/ml) and to a non-specific immunotoxin, hIgG-ZZ-PE38 (data not shown).

Taken together, these results indicate that by exploiting the high specificity of CD24 for cancerous cells, on the one hand, and the anti-cancer effects of anti-CD24 immunotherapy on the other, un armed-anti-CD24 antibody allows selective binding and efficient killing of cancer cells without harming normal cells, indicating that the SWA11-ZZ-PE38 immunoconjugate has a valuable therapeutic potential for the treatment of cancers, and particularly colorectal and pancreatic.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

CITED PUBLICATIONS

1. Vogelstein B, Fearon E R, Hamilton S R, et al. Genetic alterations during colorectal-tumor development. N Engl J Med 1988; 319:525-32.
2. Arnold C N, Goel A, Blum H E, Boland C R. Molecular pathogenesis of colorectal cancer: implications for molecular diagnosis. Cancer 2005; 104:2035-47.
3. Kristiansen G, Sammar M, Altevogt P. Tumor biological aspects of CD24, a mucin-like adhesion molecule. Journal of Molecular Histology 2004; 35:255-62.
4. Kristiansen G, Winzer K J, Mayordomo E, et al. CD24 expression is a new prognostic marker in breast cancer. Clin Cancer Res 2003b; 9:4906-13.
5. Kristiansen G, Schluns K, Yongwei Y, Denkert C, Dietel M, Petersen I. CD24 is an independent prognostic marker of survival in nonsmall cell lung cancer patients. Br J Cancer 2003a; 88:231-6.
6. Kristiansen G, Denkert C, Schluns K, Dahl E, Pilarsky C, Hauptmann S. CD24 is expressed in ovarian cancer and is a new independent prognostic marker of patient survival. Am J Pathol 2002; 161:1215-21.
7. Kristiansen G, Pilarsky C, Pervan J, et al. CD24 expression is a significant predictor of PSA relapse and poor prognosis in low grade or organ confined prostate cancer. Prostate 2004; 58:183-92.
8. Sagiv E., Memeo L., Karin A., et al. CD24 is a new oncogene, early at the multi-step process of colorectal cancer carcinogenesis. Gastroenterology 2006; 131:630-9.
9. Suzuki T, Kiyokawa N, Taguchi T, Sekino T, Katagiri Y U, Fujimoto J. CD24 induces apoptosis in human B cells via the glycolipidenriched membrane domains/rafts-mediated signaling system. J Immunol 2001; 166:5567-77.
10. Kadmon G, Von Bohlen, Halbach F, Schachner M, Altevogt P. LFA-1-sensitive effects of antibodies to nectadrin, the heat stable antigen, on B-lymphoblast aggregation and signal transduction. Biochem Biophys Res Commun 1994; 198:1209-15.
11. Poncet C, Frances V, Gristina R, Scheiner C, Pellissier J F, Figarella-Branger D. CD24, a glycosylphosphatidylinositol-anchored molecule, is transiently expressed during the development of human central nervous system and is a marker of human neural cell lineage tumors. Acta Neuropathol 1996; 91:400-8.
12. Jacob J, Bellach J, Grutzmann R, et al. Expression of CD24 in adenocarcinomas of the pancreas correlates with higher tumor grades. Pancreatology 2004; 4:454-60.
13. Fischer G F, Majdic O, Gadd S, Knapp W. Signal transduction in lymphocytic and myeloid cells via CD24, a new member of phosphoinositol-anchored membrane molecules. J Immunol 1990; 144:638-41.
14. Sammar M, Aigner S, Hubbe M, et al. Heat-stable antigen (CD24) as ligand for mouse P-selectin. Int Immunol 1994; 6:1027-36.
15. Aigner S, Sthoeger Z M, Fogel M, et al. CD24, a mucin-type glycoprotein, is a ligand for P-selectin on human tumor cells. Blood 1997; 89:3385-95.
16. Aigner S, Ramos C L, Hafezi-Moghadam A, et al. CD24 mediates rolling of breast carcinoma cells on P-selectin. FASEB J 1998; 12:1241-51.
17. Schabath H, Runz S, Joumaa S, Altevogt P. CD24 affects CXCR4 function in pre-B lymphocytes and breast carcinoma cells. J Cell Sci 2006; 119:314-25.
18. Chappel M S, Hough M R, Mittel A, Takei F, Kay R, Humphries R K. Cross-linking the murine heat-stable antigen induces apoptosis in B cell precursors and suppresses the anti-CD40-induced proliferation of mature resting B lymphocytes. J Exp Med 1996; 184:1638-49.
19. Taguchi T, Kiyokawa N, Mimori K, et al. Pre-B cell antigen receptor-mediated signal inhibits CD24-induced apoptosis in human pre-B cells. J Immunol 2003; 170:252-60.
20. Sagiv E, Kazanov D and Arber N. CD24 plays an important role in the carcinogenesis process of the pancreas. Biomed Pharmacother 2006; 60:280-4.
21. Baumann P, Cremers N, Kroese F, et al. CD24 expression causes the acquisition of multiple cellular properties associated with tumor growth and metastasis. Cancer Res 2005; 65:10783-93.
22. Smith S C, Oxford G, Wu Z, et al. The metastasis-associated gene CD24 is regulated by Ral GTPase and is a mediator of cell proliferation and survival in human cancer. Cancer Res 2006; 66:1917-22.
23. Brummelkamp T R, Bernards R, Agami R. Stable suppression of tumorigenicity by virus-mediated RNA interference. Cancer Cell 2002; 2:243-50.
24. Aigner S, Ruppert M, Hubbe M, et al. Heat stable antigen (mouse CD24) supports myeloid cell binding to endothelial and platelet P-selectin. Int Immunol 1995; 7:1557-65.
25. Kim Y J, Borsig L, Varki N M, Varki A. P-selectin deficiency attenuates tumor growth and metastasis. Proc Natl Acad Sci USA 1998; 95:9325-30.
26. Zarn J A, Zimmermann S M, Pass M K, Waibel R, Stahel R A. Association of CD24 with the kinase c-fgr in a small cell lung cancer cell line and with the kinase lyn in an erythroleukemia cell line. Biochem Biophys Res Commun 1996; 225:384-91.
27. Jung K C, Park W S, Kim H J, et al. TCR-independent and caspase-independent apoptosis of murine thymocytes by CD24 cross-linking. J Immunol 2004; 172:795-802.
28. Runz S, Mierke C T, Jouma S, Behrens J, Fabry B, Altevogt P. CD24 induces localization of beta1 integrin to lipid raft domains. Biochem Biophys Res Commun 2008; 365: 35-41.
29. Brockhausen I. Mucin-type O-glycans in human colon and breast cancer: glycodynamics and functions. EMBO Rep 2006; 7:599-604.
30. Kazanov D, Shapira I, Pick M, Kolker O, Liberman E, Deutsch V, Strier L, Dvory-Sobol H, Kunik T, Arber N. Oncogenic transformation of normal enterocytes by overexpression of cyclin D1. Dig Dis. Sci 2003; 48:1251-61.
31. Real P J, Sanz C, Gutierrez O, Pipaon C, Zubiaga A M, Fernandez-Luna J L. Transcriptional activation of the proapoptotic bik gene by E2F proteins in cancer cells. FEBS Lett 2006; 580: 5905-9.

What is claimed is:

1. A chimeric antibody comprising a scFv having the amino acid sequence as set forth in SEQ ID NO: 21 and wherein said antibody binds an extracellular epitope of a CD24 polypeptide.

2. The antibody of claim 1, wherein said antibody further comprises a human Fc domain.

3. A pharmaceutical composition comprising as active ingredients the antibody of claim 1 and a chemotherapeutic agent, and a pharmaceutically acceptable carrier.

4. A pharmaceutical composition comprising as an active ingredient the antibody of claim 2, and a pharmaceutically acceptable carrier.

5. The pharmaceutical composition of claim 3, wherein said chemotherapeutic agent is attached to said antibody.

6. The pharmaceutical composition of claim 4, further comprising a chemotherapeutic agent.

7. The pharmaceutical composition of claim 6, wherein said chemotherapeutic agent is attached to said antibody.

8. A method of inhibiting growth of cancer cells, the method comprising contacting said cancer cells with a therapeutic amount of the antibody of claim 1, wherein said cancer cells express CD24.

9. The method of claim 8, further comprising contacting said cancer cells with a chemotherapeutic agent, and wherein said chemotherapeutic agent is exclusive of doxorubicin.

10. The method of claim 8, wherein said cancer cells are colorectal cancer cells or pancreatic cancer cells expressing CD24.

11. The method of claim 9, wherein said chemotherapeutic agent is attached to said antibody, and wherein said chemotherapeutic agent is exclusive of doxorubicin.

12. The method of claim 11, wherein said cancer cells are colorectal cancer cells or pancreatic cancer cells expressing CD24.

13. The method of claim 11, wherein said cancer cells are of a subject and said subject is diagnosed with colorectal cancer or pancreatic cancer expressing CD24.

14. A method of treating growth of cancer cells expressing CD24 in a subject in need thereof, the method comprising administering to said subject a therapeutic amount of the pharmaceutical composition of claim 4, thereby treating growth of said cancer cells expressing CD24 in said subject.

15. The method of claim 14, wherein said subject is diagnosed with colorectal cancer or pancreatic cancer expressing CD24.

16. A method of treating growth of cancer cells expressing CD24 in a subject in need thereof, the method comprising administering to said subject a therapeutic amount of the pharmaceutical composition of claim 5, thereby treating growth of said cancer cells in said subject.

17. The method of claim 16, wherein said subject is diagnosed with colorectal cancer or pancreatic cancer expressing CD24.

18. A method of treating growth of cancer cells expressing CD24 in a subject in need thereof, the method comprising administering to said subject a therapeutic amount of the pharmaceutical composition of claim 6, thereby treating growth of said cancer cells expressing CD24 in said subject.

19. The method of claim 18, wherein said subject is diagnosed with colorectal cancer or pancreatic cancer expressing CD24.

* * * * *

SEQUENCE LISTING

<160> NUMBER OF SEQ ID NOS: 28

<210> SEQ ID NO 1
<211> LENGTH: 15
<212> TYPE: PRT
<213> ORGANISM: Artificial sequence
<220> FEATURE:
<223> OTHER INFORMATION: N' terminal sequnce of VH SWA11

<400> SEQUENCE: 1

Asp Val Gln Leu Gln Glu Ser Gly Pro Asp Leu Val Lys Pro Ser
1               5                   10                  15

<210> SEQ ID NO 2
<211> LENGTH: 23
<212> TYPE: PRT
<213> ORGANISM: Artificial sequence
<220> FEATURE:
<223> OTHER INFORMATION: N' terminal sequnce of VL SWA11

<400> SEQUENCE: 2

Asp Ile Val Met Ser Gln Ser Pro Ser Ser Leu Asn Val Ser Val Gly
1               5                   10                  15

Glu Lys Val Thr Met Arg Cys
            20

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 3
cagggaaata acccttgacc aggc                                          24

<210> SEQ ID NO 4
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 4
ggggtagaag ttgttcaaga agc                                           23

<210> SEQ ID NO 5
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 5
agccggccat ggccgatgtg caccttcagg agtcagg                            37

<210> SEQ ID NO 6
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 6
ggctccgata tcgtgatgtc acagtctcca tcc                                33

<210> SEQ ID NO 7
<211> LENGTH: 118
<212> TYPE: PRT
<213> ORGANISM: Artificial sequence
<220> FEATURE:
<223> OTHER INFORMATION: VH domain C terminus

<400> SEQUENCE: 7

Asp Val His Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Thr Trp His Trp Ile Arg Gln Phe Pro Gly Asn Thr Val Glu Trp
        35                  40                  45

Met Gly Tyr Ile Gln Tyr Thr Gly Ser Thr Arg Tyr Asn Pro Ala Leu
    50                  55                  60

Arg Gly Arg Leu Ser Ile Ser Arg Asp Thr Ser Lys Asn Gln Phe Phe
65                  70                  75                  80

Leu Gln Leu Ile Ser Val Thr Thr Ala Asp Thr Gly Thr Tyr Phe Cys
                85                  90                  95

Ala Arg Gly Thr Thr Ala Ser Phe Asp Tyr Trp Gly Gln Gly Thr Thr
            100                 105                 110

Leu Thr Val Ala Ser Ala
        115

<210> SEQ ID NO 8
<211> LENGTH: 113
<212> TYPE: PRT
<213> ORGANISM: Artificial sequence
<220> FEATURE:
<223> OTHER INFORMATION: VK domain C-terminus

<400> SEQUENCE: 8

Asp Ile Val Met Ser Gln Ser Pro Ser Ser Leu Asn Val Ser Val Gly
1               5                   10                  15

Glu Lys Val Thr Met Arg Cys Arg Ser Ser Gln Ser Leu Leu Tyr Ser
            20                  25                  30

Ser Asp Gln Lys Asn Tyr Leu Thr Trp Tyr Gln Gln Lys Pro Gly Gln
        35                  40                  45

Ser Pro Lys Leu Leu Ile Ser Trp Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Gly Val Tyr Tyr Cys Gln Gln
                85                  90                  95

Tyr Phe Ile Tyr Pro Leu Thr Phe Gly Val Gly Thr Lys Leu Gly Leu
            100                 105                 110

Lys

<210> SEQ ID NO 9
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 9
cttggtgcta gcggctgagg cgactgtgag agtgg                          35

<210> SEQ ID NO 10
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 10
ccacaggcgc gcactccgat gtgcaccttc aggagtcagg        40

<210> SEQ ID NO 11
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 11
agccaccgta cgtttcagcc ccagcttggt ccc        33

<210> SEQ ID NO 12
<211> LENGTH: 465
<212> TYPE: PRT
<213> ORGANISM: Artificial sequence
<220> FEATURE:
<223> OTHER INFORMATION: Humanized SWA11 IgH amino acid sequence

<400> SEQUENCE: 12

```
Met Gly Asp Asn Asp Ile His Phe Ala Phe Leu Ser Thr Gly Ala His
1               5                   10                  15

Ser Asp Val His Leu Gln Glu Ser Gly Pro Asp Leu Val Lys Pro Ser
            20                  25                  30

Gln Ser Leu Ser Leu Thr Cys Thr Val Thr Gly Tyr Ser Ile Thr Ser
        35                  40                  45

Gly Tyr Thr Trp His Trp Ile Arg Gln Phe Pro Gly Asn Thr Val Glu
    50                  55                  60

Trp Met Gly Tyr Ile Gln Tyr Thr Gly Ser Thr Arg Tyr Asn Pro Ala
65                  70                  75                  80

Leu Arg Gly Arg Leu Ser Ile Ser Arg Asp Thr Ser Lys Asn Gln Phe
                85                  90                  95

Phe Leu Gln Leu Ile Ser Val Thr Thr Ala Asp Thr Gly Thr Tyr Phe
            100                 105                 110

Cys Ala Arg Gly Thr Thr Ala Ser Phe Asp Tyr Trp Gly Gln Gly Thr
        115                 120                 125

Thr Leu Thr Val Ala Ser Ala Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Arg Pro
```

```
                            245                 250                 255
Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 13
<211> LENGTH: 1398
<212> TYPE: DNA
<213> ORGANISM: Artificial sequence
<220> FEATURE:
<223> OTHER INFORMATION: Humanized SWA11 IgH coding DNA sequence

<400> SEQUENCE: 13
atgggtgaca atgacatcca ctttgccttt ctctccacag gcgcgcactc cgatgtgcac      60
cttcaggagt caggacctga cctggtgaaa ccttctcagt cactttcact cacctgcact     120
gtcactggct actccatcac cagtggttat acctggcact ggatccggca gtttccagga     180
aacacagtgg aatggatggg ctacatacag tacactggtt ccactaggta caaccccgct     240
ctcagaggtc gactctctat cagtcgagac acatccaaga ccagttcttc ctgcagttg      300 atttctgtga ctactgcgga cacaggcaca tatttctgtg caaggggtac tacggcctcc     360
tttgactact ggggccaagg caccactctc acagtcgcct cagccgctag caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagagagttg agcccaaatc ttgtgacaaa     720
actcacacat gcccaccgtg cccagcacct gaactcctgg ggagaccgtc agtcttcctc     780
```

```
ttcccccaa aacccaagga caccctcatg atctcccgga ccctgaggt cacatgcgtg    840 gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac acaggtgta caccctgccc ccatcccggg aggagatgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctatagcaa gctcaccgtg gacaagagca ggtggcagca ggggaacgtc   1320
ttctcatgct ccgtgatgca tgaggctctg cacaaccact acacgcagaa gagcctctcc   1380
ctgtccccgg gtaaatga                                                   1398
```

<210> SEQ ID NO 14
<211> LENGTH: 236
<212> TYPE: PRT
<213> ORGANISM: Artificial sequence
<220> FEATURE:
<223> OTHER INFORMATION: Humanized SWA11 IgL amino acid sequence

<400> SEQUENCE: 14

```
Gly Asp Asn Asp Ile His Phe Ala Phe Leu Ser Thr Gly Ala His Ser
1               5                   10                  15

Asp Ile Val Met Ser Gln Ser Pro Ser Ser Leu Asn Val Ser Val Gly
            20                  25                  30

Glu Lys Val Thr Met Arg Cys Arg Ser Ser Gln Ser Leu Leu Tyr Ser
        35                  40                  45

Ser Asp Gln Lys Asn Tyr Leu Thr Trp Tyr Gln Gln Lys Pro Gly Gln
    50                  55                  60

Ser Pro Lys Leu Leu Ile Ser Trp Ala Ser Thr Arg Ala Ser Gly Val
65                  70                  75                  80

Pro Asp Arg Phe Thr Gly Ser Gly Ser Gly Thr Asp Phe Thr Leu Thr
                85                  90                  95

Ile Ser Ser Val Lys Ala Glu Asp Leu Gly Val Tyr Tyr Cys Gln Gln
            100                 105                 110

Tyr Phe Ile Tyr Pro Leu Thr Phe Gly Val Gly Thr Lys Leu Gly Leu
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 15
<211> LENGTH: 714

```
<212> TYPE: DNA
<213> ORGANISM: Artificial sequence
<220> FEATURE:
<223> OTHER INFORMATION: Humanized SWA11 IgL coding DNA sequence

<400> SEQUENCE: 15
atgggtgaca atgacatcca ctttgccttt ctctccacag gcgcgcactc cgatatcgtg      60
atgtcacagt ctccatcctc cctaaatgtg tcagttggag agaaggttac tatgaggtgc     120
aggtccagtc agagcctttt atatagtagc gatcaaaaga actacttgac ctggtaccag     180
cagaaacctg gcagtctccc taaattgctg atttcctggg catccactag gcatctgggg     240
gtccctgatc gcttcacagg cagtggatct gggacagatt tcactctcac catcagcagt     300
gtgaaggctg aagacctggg agtttattac tgtcaacaat attttatcta ccgctcacg      360
ttcggtgttg ggaccaagct ggggctgaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttaa           714

<210> SEQ ID NO 16
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 16
gccggccatg gccgatgtgc accttcagga gtcagg                                36

<210> SEQ ID NO 17
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 17
tcctcctgct gagccggctg aggcgactgt gagag                                 35

<210> SEQ ID NO 18
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 18
ggctccgata tcgtgatgtc acagtctcc                                        29

<210> SEQ ID NO 19
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 19
ccacctgcgg ccgctttcag ccccagcttg gtccc                                 35
```

```
<210> SEQ ID NO 20
<211> LENGTH: 13
<212> TYPE: PRT
<213> ORGANISM: Artificial sequence
<220> FEATURE:
<223> OTHER INFORMATION: A flexible linker for linking VH and VL domains
      of humanized SWA11 scFv

<400> SEQUENCE: 20

Gly Gly Ser Gly Gly Gly Gly Ser Gly Gly Gly Gly Ser
1               5                   10

<210> SEQ ID NO 21
<211> LENGTH: 423
<212> TYPE: PRT
<213> ORGANISM: Artificial sequence
<220> FEATURE:
<223> OTHER INFORMATION: Humanized SWA11 scFv amino acid sequence

<400> SEQUENCE: 21

Met Ala Asp Val His Leu Gln Glu Ser Gly Pro Asp Leu Val Lys Pro
1               5                   10                  15

Ser Gln Ser Leu Ser Leu Thr Cys Thr Val Thr Gly Tyr Ser Ile Thr
            20                  25                  30

Ser Gly Tyr Thr Trp His Trp Ile Arg Gln Phe Pro Gly Asn Thr Val
        35                  40                  45

Glu Trp Met Gly Tyr Ile Gln Tyr Thr Gly Ser Thr Arg Tyr Asn Pro
    50                  55                  60

Ala Leu Arg Gly Arg Leu Ser Ile Ser Arg Asp Thr Ser Lys Asn Gln
65                  70                  75                  80

Phe Phe Leu Gln Leu Ile Ser Val Thr Ala Asp Thr Gly Thr Tyr
                85                  90                  95

Phe Cys Ala Arg Gly Thr Thr Ala Ser Phe Asp Tyr Trp Gly Gln Gly
            100                 105                 110

Thr Thr Leu Thr Val Ala Ser Ala Gly Ser Ala Gly Gly Gly Ser
        115                 120                 125

Gly Gly Gly Gly Ser Gly Gly Gly Ser Asp Ile Val Met Ser Gln
    130                 135                 140

Ser Pro Ser Ser Leu Asn Val Ser Val Gly Glu Lys Val Thr Met Arg
145                 150                 155                 160

Cys Arg Ser Ser Gln Ser Leu Leu Tyr Ser Asp Gln Lys Asn Tyr
                165                 170                 175

Leu Thr Trp Tyr Gln Gln Lys Pro Gly Gln Ser Pro Lys Leu Leu Ile
            180                 185                 190

Ser Trp Ala Ser Thr Arg Ala Ser Gly Val Pro Asp Arg Phe Thr Gly
        195                 200                 205

Ser Gly Ser Gly Thr Asp Phe Thr Leu Thr Ile Ser Ser Val Lys Ala
    210                 215                 220

Glu Asp Leu Gly Val Tyr Tyr Cys Gln Gln Tyr Phe Ile Tyr Pro Leu
225                 230                 235                 240

Thr Phe Gly Val Gly Thr Lys Leu Gly Leu Lys Ala Ala Ala Gly Gly
                245                 250                 255

Ala Asn Thr Pro Val Ser Gly Asn Leu Lys Val Glu Phe Tyr Asn Ser
            260                 265                 270

Asn Pro Ser Asp Thr Thr Asn Ser Ile Asn Pro Gln Phe Lys Val Thr
        275                 280                 285

Asn Thr Gly Ser Ser Ala Ile Asp Leu Ser Lys Leu Thr Leu Arg Tyr
    290                 295                 300
```

```
Tyr Tyr Thr Val Asp Gly Gln Lys Asp Gln Thr Phe Trp Ala Asp His
305                 310                 315                 320

Ala Ala Ile Ile Gly Ser Asn Gly Ser Tyr Asn Gly Ile Thr Ser Asn
            325                 330                 335

Val Lys Arg Thr Phe Val Lys Met Ser Ser Thr Asn Asn Ala Asp
        340                 345                 350

Thr Tyr Leu Glu Ile Ser Phe Thr Gly Gly Thr Leu Glu Pro Gly Ala
        355                 360                 365

His Val Gln Ile Gln Gly Arg Phe Ala Lys Asn Asp Trp Ser Asn Tyr
370                 375                 380

Thr Gln Ser Asn Asp Tyr Ser Phe Lys Ser Ala Ser Gln Phe Val Glu
385                 390                 395                 400

Trp Asp Gln Val Thr Ala Tyr Leu Asn Gly Val Leu Val Trp Gly Lys
                405                 410                 415

Glu Pro Gly Gly Ser Val Val
                420

<210> SEQ ID NO 22
<211> LENGTH: 1277
<212> TYPE: DNA
<213> ORGANISM: Artificial sequence
<220> FEATURE:
<223> OTHER INFORMATION: Humanized SWA11 scFv coding DNA sequence

<400> SEQUENCE: 22
atggccgatg tgcaccttca ggagtcagga cctgacctgg tgaaccttc tcagtcactt        60 tcactcacct gcactgtcac tggctactcc atcaccagtg ttatacctg cactggatc       120 cggcagtttc caggaaacac agtggaatgg atgggctaca tacagtacac tggttccact      180
aggtacaacc ccgctctcag aggtcgactc tctatcagtc gagacacatc caagaaccag      240
ttcttcctgc agttgatttc tgtgactact gcggacacag gcacatattt ctgtgcaagg      300
ggtactacgg cctcctttga ctactgggc caaggcacca ctctcacagt cgcctcagcc       360
ggctcagcag gaggaggagg atccggtggt ggtggttctg gcggcggcgg ctccgatatc      420
gtgatgtcac agtctccatc ctccctaaat gtgtcagttg agagaaggt tactatgagg       480 tgcaggtcca gtcagagcct tttatatagt agcgatcaaa agaactactt gacctggtac      540
cagcagaaac ctgggcagtc tcctaaattg ctgatttcct gggcatccac tagggcatct      600
ggggtccctg atcgcttcac aggcagtgga tctgggacag atttcactct caccatcagc      660
agtgtgaagg ctgaagacct gggagtttat tactgtcaac aatatttat ctatccgctc       720 acgttcggtg ttgggaccaa gctggggctg aaagcggccg caggtggcgc aaatacaccg      780
gtatcaggca atttgaaggt tgaattctac aacagcaatc cttcagatac tactaactca      840
atcaatcctc agttcaaggt tactaatacc ggaagcagtg caattgattt gtccaaactc      900
acattgagat attattatac agtagacgga cagaaagatc agaccttctg gctgaccat      960 gctgcaataa tcggcagtaa cggcagctac aacggaatta cttcaaatgt aaaaagaaca     1020
tttgtaaaaa tgagttcctc aacaaataac gcagacacct accttgaaat aagctttaca     1080
ggcggaactc ttgaaccggg tgcacatgtt cagatacaag gtagatttgc aaagaatgac     1140
tggagtaact atacacagtc aaatgactac tcattcaagt ctgcttcaca gtttgttgaa     1200
tgggatcagg taacagcata cttgaacggt gttcttgtat ggggtaaaga accggtggc     1260 agtgtagtat aggatcc                                                   1277

<210> SEQ ID NO 23
```

```
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 23
gatatacata tggatgtgca ccttcaggag tcagg                              35

<210> SEQ ID NO 24
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 24
ctccggaagc tttcagcccc agcttggtcc c                                  31

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
ggagattgtt gccatcaacg                                               20

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
ttggtggtgc aggatgcatt                                               20

<210> SEQ ID NO 27
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 27
ggcactgctc ctacccacgc ag                                            22

<210> SEQ ID NO 28
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 28
gccacattgg aattccagac gcc                                           23
```